(12) United States Patent
Foley et al.

(10) Patent No.: US 6,224,775 B1
(45) Date of Patent: *May 1, 2001

(54) METHOD OF SEPARATING CHEMICAL MIXTURES

(75) Inventors: Joe P. Foley, Chadds Ford, PA (US); Sally J. Grieb, Kent (GB)

(73) Assignee: Villanova University, Villanova, PA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/146,399

(22) Filed: Sep. 3, 1998

Related U.S. Application Data (60) Provisional application No. 60/058,146, filed on Sep. 8, 1997.

(51) Int. Cl.[7] ................................................. B01D 15/08
(52) U.S. Cl. ........................ 210/635; 210/656; 210/748; 210/198.2; 204/455
(58) Field of Search .................................. 210/635, 656, 210/748, 198.2, 243, 502.1; 204/451, 455, 601, 605; 53/473

(56) References Cited

U.S. PATENT DOCUMENTS

| | | | |
|---|---|---|---|
| 5,202,433 | * | 4/1993 | Okamoto ............................. 540/200 |
| 5,229,002 | * | 7/1993 | Namikoshi ........................... 210/635 |
| 5,296,618 | * | 3/1994 | Aaltonen ............................. 549/542 |
| 5,453,163 | * | 9/1995 | Yan .................................... 210/656 |
| 5,811,532 | * | 9/1998 | House ................................. 210/635 |

OTHER PUBLICATIONS

H. Rebscher/U. Pyell "Instrumental Developments in Capillary Electrochromatography", Chromatographia vol. 42, No. 3/4, Feb. 1996, pp. 171–176.

Beate Behnke, Edgar Grom, Ernst Bayer, "Evaluation of the parameters determining the performance of electrochromatography in packed capillary columns", Journal of Chromatography A, 716 (1995) 207–213.

(List continued on next page.)

*Primary Examiner*—Ernest G. Therkorn
(74) *Attorney, Agent, or Firm*—Schnader Harrison Segal & Lewis LLP (57) ABSTRACT

A method for separating a mixture of at least two chemical compounds which first involves loading and sintering a frit material in a capillary to form a first retaining frit. After removing substantially all unsintered frit material from the capillary, a packing material made up of a substrate coated with a linear carbohydrate polymer is loaded into the capillary adjacent to the first retaining frit to form a stationary phase. More frit material is loaded in the capillary and is sintered to form a second retaining frit adjacent to the packing material on the side opposite from the first retaining frit. Substantially all unsintered frit material is again removed from the capillary. The chemical mixture is then introduced into the capillary at one of the retaining frits, and migration of the mixture across the packing material is induced by applying a voltage across the capillary. Differences in electroosmotic flow velocity between the compounds cause them to separate during migration.

16 Claims, 6 Drawing Sheets

OTHER PUBLICATIONS

Jia–Li Liao, Nong Chen, Christer Ericson and Stellan Hjerten, "Preparation of Continuous Beds Derivatized with One–Step Alkyl and Sulfonate Groups for Capillary Electrochromatography", Anal. Chem 1996, 68, 3468–3472.

Chuzo Fujimoto, Yutake Fujise, and Ejji Matsuzawa, "Fritless packed Columns for Capillary Electrochromatography: Separation of Uncharged Compounds on Hydrophobic Hydrogels", Anal. Chem. 1996, 68, 2753–2757.

R.J. Boughtflower, T. Underwood, and C.J. Paterson, "Capillary Electrochromatography—Some Important Considerations in the Preparation of Packed Capillaries and the Choice of Mobile Phase Buffers", Chromatographia vol. 40, No. 5/6, Mar. 1995 329–335.

Chao Yan, Rajeev Dadoo, Hui Zhao, and Richard N. Zare, "Capillary Electrochromatography: Analysis of Polycyclic Aromatic Hydrocarbons", Analytical Chemistry, vol. 67, No. 13, Jul. 1, 1995 2026–2029.

Hideko Yamamoto, Joseph Baumann and Fritz Erni, "Electrokinetic reversed–phase chromatography with packed capillaries", Chromsymp, 2495, 313–319.

Maria T. Dulay, David J. Rakestraw, Richard N. Zare, "Automated capillary electrochromatography: reliability and reproducibility studies" Journal of Chromatography A. 725, (1996) 361–366.

Monika M. Dittmann, Klaus Wienand, Fritz Bek, Gerard P. Rozing, "Theory and Practice of Capillary Electrochromatography" vol. 13, No. 10 Oct. 1995, 800–814.

Mark M. Robson, Maria G. Cikalo, Peter Myers, Melvin R. Euerby, Keigh D. Bartle, "Capillary Electrochromatography: A Review", 1997 John Wiley & Sons, Inc., pp. 357–372.

Anders Palm and Miles V. Novotny, "Macroporous Polyacrylamide/Poly(ethylene glycol) Matrixes as Stationary Phases in Capillary Electrochromatography", Anal. Chem 1997, 69, 4499–4507.

Daming Li and Vincent T. Remcho, "Perfusive Electroosmotic Transport in Packed Capillary Electrochromatography: Mechanism and Utility", 1997 John Wiley & Sons, Inc., pp. 389–397.

Song Li and David K. Lloyd, "Direct Chiral Separations by Capillary elctrophoresis Using Capillaries Packed with an $_\alpha$1–Acid Glycoprotein Chiral Stationary Phase", Anal. Chem. vol. 65, No. 24, Dec. 15, 1993, 3684–3690.

Wintergreen Conference Center, "Nineteenth International Symposium on Capillary Chromatography and Electrophoresis", May 18–22, 1997, pp. 60–95.

Chao Yan, Daniel Schaufelberger, and Fritz Erni, "Electrochromatography and micro high–performance liquid chromatography with 320 $\mu$m I.D. packed columns", Journal of Chromatography A. 670 (1994) 15–23.

Christer Ericson, Jia–Li Liao, Ken'ichi Nakazato, and Stellan Hjerten, "Preparation of continuous beds for electrochromatography and reversed–phase liquid chromatography of low–molecular–mass compound", Journal of Chromatography A, 767, (1997) 33–41.

G.A. Lord, D.B. Gordon, P. Myers, and B.W. King "Tapers and restrictors for capillary electrochromatography and capillary electrochromatography–mass spectrometry", Journal of Chromatography A, 768 (1997) 9–16.

Frederic Lelievre, Chao Yan, Richard N. Zare and P. Gariel, "Capillary electrochromatography: operating charactereistics and enantiomeric separations", Journal of Chromatography A, 723 (1996) 145–156.

M.M. Robson, S. Roulin, S.M. Shariff, M.W. Raynor, K.D. Bartle, A.A> Clifford, P. Myers, M.R. Euerby, and C.M. Johnson, "Capillary Electrochromatography Using Columns Packed with a Supercritical Fluid Carrier", Chromatographia vol. 43, No. 5/6 Sep. 1996, 313–321.

S.E. van den Bosch, S. Heemstra, J.C. Kraak, and H. Poppe, "Experiences with packed capillary electrochromatography at ambient pressure", Journal of Chromatography A, 755 (1996) 165–177.

Francotte, E. and Jung, M., "Enantiomer Separation by Open–Tubular Liquid Chromatography and Electrochromatography in Cellulose–Coated Capillaries" Chromatographia v42, No. 42, May 1996, pp. 521–527.

* cited by examiner

METHOD OF SEPARATING CHEMICAL MIXTURES

This application claims the benefit of U.S. Provisional Application Ser. No. 60/058,146, filed Sep. 8, 1997.

FIELD OF THE INVENTION

The invention relates to a method of separating chemical mixtures. More particularly, the invention relates to a method of separating chiral and achiral chemical mixtures through capillary electrochromatography wherein an immobilized carbohydrate polymer is used as a chemical selector.

BACKGROUND OF THE INVENTION

Capillary electrochromatography (CEC) is a hybrid method of capillary electrophoresis (CE) and high performance liquid chromatography (HPLC). Though CEC was first demonstrated more than two decades ago, the advent of sophisticated CE instrumentation, expanded use and understanding of CE, and the continuing quest for more efficient separation methods has recently intensified interest in CEC.

CEC involves the application of an electric field between the ends of a 50–110 µm capillary containing a stationary phase. "Open tubular" CEC describes a technique where the stationary phase is bonded to the capillary wall, while "packed" CEC describes a method involving capillaries filled either with a polymer gel stationary phase or a small particle (about 1–10 µm) silica-based stationary phase.

Figure 1:
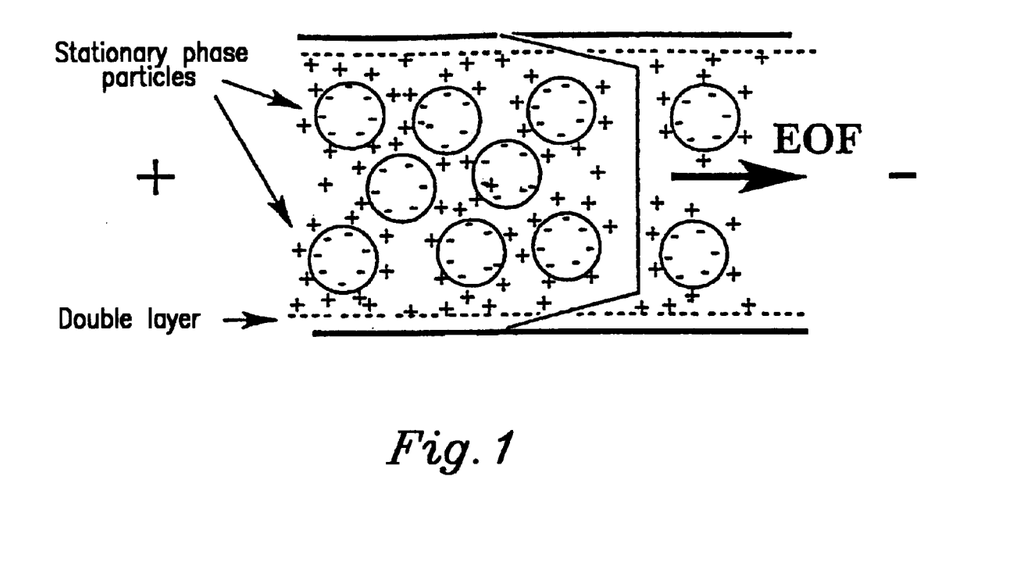
FIG. 1 is a schematic representation of a standard flow profile produced during CEC.

In all CEC techniques, a liquid phase is transported through the capillary by electroosmosis or a combination of electroosmosis and pressure, and solutes are separated based on their partitioning between the stationary and mobile phases and on their charge to frictional drag. As shown in FIG. 1, the electroosmotic flow originates from the electrical double layer at the surface of the stationary phase as well as the capillary wall and generates a plug-like flow profile which is independent of the geometry and size of the channels between the particles. This phenomenon can provide very high efficiencies, limited primarily by the solute diffusion coefficient.

In contrast to capillary liquid chromatography, CEC can utilize long capillaries of small, very efficient particles since there is no column back pressure. It has been shown in Dittmann et al., $LC$-$GC$, 13: 800 (1995) that CEC has the potential to provide column plate numbers 5 to 10 times greater than HPLC columns. The high efficiencies attainable make CEC a very attractive technique for chiral separations since it is theoretically possible to obtain baseline resolution for solutes with very small enantioselectivities.

Polysaccharide derivatives coated onto porous derivatized silica have proven to be among the most versatile and widely used chiral stationary phases in HPLC. They have been used in both normal and reversed phase mode and have shown extremely high enantioselectivity for many solutes. Unfortunately, unlike several other chiral selectors, their use as buffer additives in CE is precluded by their poor solubility in suitable electrolytes and high UV cut-off. However, these characteristics do not preclude their use as chiral stationary phases in CEC, and open tubular electrochromatography using 50 µm I.D. fused silica capillaries coated with a cellulose derivative has been investigated by E. Francotte and M. Jung, $Chromatographia$, 42: 521–527 (1996). Resolution was found to be heavily dependent on the thickness of the coating, and the highest efficiency achieved was a disappointingly low 60,000 plates/m.

OBJECTS OF THE INVENTION

Accordingly, it is an object of the invention to provide a novel capillary electrochromatographic separation method which provides improved resolutions, particularly for chiral separations.

Other objects will become apparent from the following description of the invention.

SUMMARY OF THE INVENTION

The invention is a chemical separation method involving capillary electrochromatography (CEC) or a combination of CEC and capillary liquid chromatography (CLC). The method comprises packing a capillary, preferably a fused silica capillary, with a packing material, preferably silica particles. The packing material is coated with one or more linear carbohydrate polymer chiral selectors, preferably cellulose, cellulose derivatives, amylose and/or amylose derivatives, and more preferably cellulose tris(3,5-dimethylphenylcarbamate).

The packing process first involves loading a frit material into the capillary, the frit material being distinct from the packing material and preferably being an octadecyl silica product. The frit material is then sintered to form the first of two retaining frits, with the unsintered frit material thereafter being removed from the capillary. The packing material is then loaded into the capillary to form a stationary phase, with the retaining frit defining one end of the stationary phase. The packing material is preferably pumped into the capillary as a slurry at a pressure of about 430 bar or less. More frit material is then loaded and sintered to form a second retaining frit adjacent to the stationary phase at the end opposite from the first retaining frit.

A sample of analytes (a chemical mixture) is introduced into the capillary, after which a voltage is applied across the length of the capillary to achieve bulk transport of the analyte. A pressure gradient is also preferably applied to promote bulk transport of the analyte. The components (analytes) of the sample are separated during transport across the stationary phase by the differing flow velocities of the components, the component flow velocities being determined by the differing degrees of retention by the stationary phase and mass/frictional drag.

DETAILED DESCRIPTION OF THE INVENTION

We have discovered a novel CEC method of separating chiral and achiral mixtures which produces surprisingly efficient separations. In particular, the invention for the first time provides a CEC separation method which produces symmetrical peaks and reduced plate heights below four for chiral compounds. The invention can be used for the separation of charged, ionogenic or neutral chiral compounds, and all types of achiral compounds including structural isomers and other closely related compounds.

The invention utilizes one or more linear carbohydrate polymers as chemical selectors in a packed capillary format.

The linear carbohydrate polymer selector is preferably a polysaccharide, and more preferably a cellulose, cellulose derivative, amylose or amylose derivative.

One or more selectors is coated onto a substrate to form a packing material. The substrate material is not particularly limited and may be any material known in the art, and may be of any size, morphology and porosity suitable for coating and capillary packing purposes. Preferably, the substrate comprises a particulate silica product, more preferably a silylated particulate silica product, and has a preferable particle diameter of approximately 5 µm.

The capillary may be of any suitable material known in the art. Examples of capillary materials include fused silica, nylon, polyurethane, polytetrafluoroethylene, and polyethylene. Of the known capillary materials, fused silica is preferred.

An important element of the invention is the packing procedure, particularly the frit formation. The frits are sintered into the inlet and outlet of the capillary to hold the packing material, thereby holding the stationary phase inside the capillary. Conventionally, the frit material has been the same as the packing material. However, the high sintering temperatures required to form the frit can melt the chemical selector coating which would negatively affect flow properties at the frit, thus reducing the separation efficiencies associated with the system. As a result, the invention utilizes materials other than the packing material for frit formation. Preferably, octadecyl silica particles are used as the frit material.

Any method known in the art for packing substrate materials coated with linear carbohydrate polymers into a capillary may be used, examples of which include moderate and high pressure slurry packing, and electrokinetic packing. One or more selector-compatible packing solvents are used in these processes, i.e., solvents that do not dissolve the selector. Preferred packing solvents included acetonitrile (ACN) and MeOH, with ACN being most preferred. Moderate packing pressures of about 430 bar or less are preferred because higher packing pressures could fracture the packing material. Fractured particles can obstruct flow pathways within the capillary, thereby creating very low flow or no flow conditions.

The mobile phase may include any compatible buffer. Organic buffers such as morpholinoethanesulfonic acid (MES), tris(hydroxymethyl)methane (TRIS) and N-2-hydroxyethylpiperazine-N'-3-propanesulfonic acid (HEPES) are preferred since they provide lower currents and reduce bubble formation.

The invention will now be described through illustrative examples. The examples are not intended to limit the scope of the invention defined in the appended claims.

EXAMPLES

In accordance with the invention, fused silica capillaries (50 µm I.D., 363 µm O.D., 50 cm length, manufactured by Polymicro Technologies of Phoenix, Ariz.) were packed with a 5 µm chiral selector of cellulose tris(3,5-dimethylphenylcarbamate) coated onto silylated silica particles (5 µm CHIRALCEL OD manufactured by Chiral Technologies of Exton, Pa.). The method used for all of the examples will now be described, with points of variation being first described generically and later specified for each example.

Figure 2:
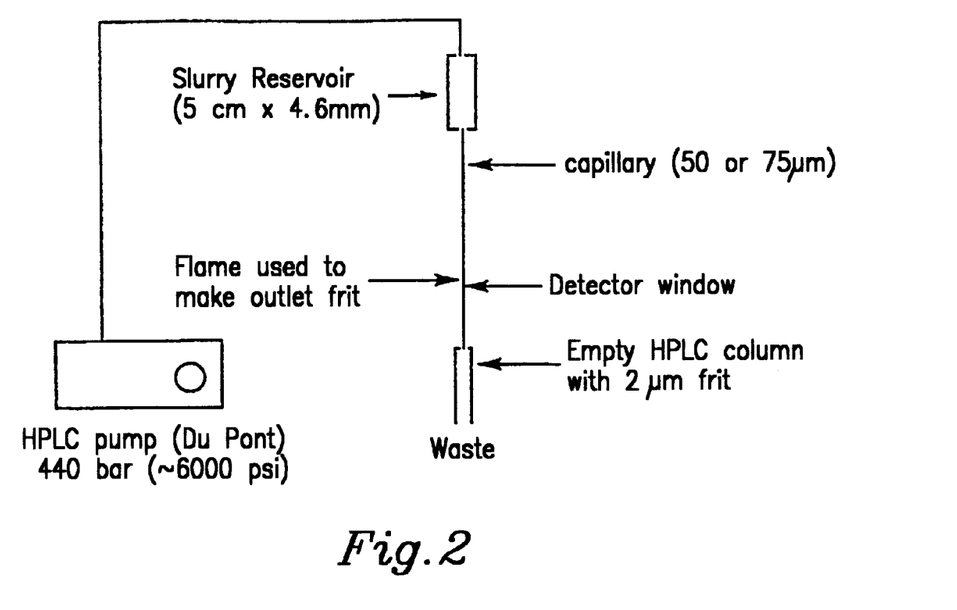
FIG. 2 is a schematic diagram of a CEC packing apparatus.

Prior to packing, a detection window of about 0.5 cm was burned in a capillary approximately 10 cm from one end. The capillary was then slurry packed at 430 bar with frit material using a HPLC pump (manufactured by DuPont Instruments, USA) connected to a 5 cm×4.6 mm reservoir loaded with a slurry of 3 µm octadecyl silica particles (3 µm Hypersil ODS2 manufactured by Hypersil of Runcorn, UK). See FIG. 2 for a schematic diagram of the apparatus. The capillary was packed with the octadecyl silica slurry to a height of approximately 5 cm above the detection window. Acetonitrile (ACN) was used as a packing solvent. After pumping the packed capillary with $H_2O$ for a few minutes, an outlet frit was produced by sintering directly above the detector window. The frit was sintered using a gas torch flame aimed through a 3 mm diameter hole in a metal sheet, whereby the packed capillary was heated for approximately 5 seconds to produce a frit with a diameter of approximately 2 mm. The octadecyl packing material on either side of the frit was then removed.

After loading the slurry reservoir of the HPLC pump with the 5 µm chiral selector and reconnecting the capillary to the slurry reservoir, the capillary was packed with the chiral selector (slowly at first so as not to blow out the formed outlet frit) to a height of approximately 25 cm. ACN was again used as a packing solvent. The packed capillary was then flushed overnight with an $ACN/H_2O$ buffer to allow the bed to pack down and form a chiral stationary phase.

Subsequently, more 3 µm octadecyl silica particles were packed on top of the chiral stationary phase, and an inlet frit was sintered from the octadecyl particles close to the chiral stationary phase in the same manner as the outlet frit. The resulting packed CEC capillary was flushed with the $ACN/H_2O$ buffer for at least 2 hours before use.

Chromatographic studies using the packed capillaries produced as described above were then undertaken using an $HP^{3D}CE$ capillary electrophoresis instrument manufactured by Hewlett Packard, Waldbronn, Germany, which can provide pressurization up to 12 bar of the inlet/outlet buffer vials. Electrolyte combinations are listed for each example. The aqueous buffer was prepared first and the pH was adjusted to various values (specified below for particular examples). The appropriate amount of acetonitrile (specified below for particular examples) was then added and the solution was mixed and thoroughly degassed by sonication and application of a vacuum for 2–3 minutes until no bubbles were observed. Once the packed CEC capillary had been installed in the capillary electrophoresis instrument, the electrolytes were changed using a high pressure flush with electroosmosis (10 bar, 10 kV) for 45 minutes. Between different inlet/outlet vials containing the same electrolyte, a short (15 minute) high pressure flush (10 bar, 10 kV) was applied. Occasionally, if the column was left unused for more than 24 hours, the capillary was reconnected to the HPLC pump and flushed using a pressure of 100 bar for 2 hours to remove any gas that may have built up. During the separation, 10 bar external pressure was applied to the inlet and outlet vials and, unless otherwise noted in specific examples, 20 kV was applied to induce electroosmotic flow. The temperature of the system was set at 22° C.

Sample solutions of 4-phenyl-2-butanol, benzoin and indapamide were prepared by dissolving them in acetonitrile (10 mg/ml) and then diluting with electrolyte to produce a 1 mg/ml solution. A small amount of thiourea was also added to define the approximate region for the appearance of a $t_o$ marker/artifact. Unless otherwise specified, injection was accomplished by electromigration, 5 kV for 10 seconds. Generally, four separations were performed, and detection was monitored at 214 nm.

Efficiencies and resolutions were provided by the Hewlett Packard CHEM STATION software and were calculated using the following equations:

$$N = 5.545(t_R/w_{0.5})^2 \text{ and } Rs = 2(t_2-t_1)/(w_1+w_2);$$

where $t_R$ is the migration time of the peak, $w_{0.5}$ is the peak width at half height, $t_1$ and $t_2$ are the migration times of the first and second enantiomers, $w_1$ and $w_2$ are the width at the base for peaks 1 and 2.

In addition, the following equations were used:

$$k'_1 = (t_1 - t_o)/t_o, \; \text{"} = k'_2/k'_1 \text{ and } h = H/d_p$$

where $k'_1$ and $k'_2$ are the capacity factors for the first and second enantiomers; $t_o$, $t_1$ and $t_2$ are the migration times of the perturbation, first enantiomer and second enantiomer, respectively; h is the reduced plate height, H is the height equivalent to a theoretical plate and dp is the particle diameter.

Example 1

Figure 3:
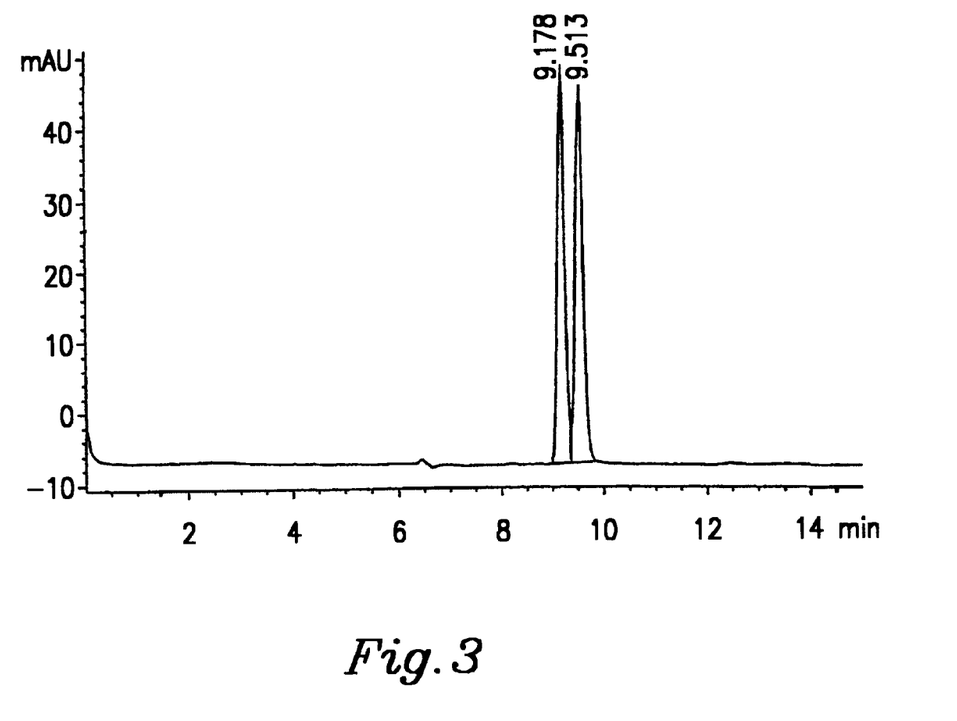
FIG. 3 is a graph of a CEC separation of 4-phenyl-2-butanol performed in accordance with the invention.

A CEC separation of 4-phenyl-2-butanol, a neutral chiral compound, was performed on a packed capillary prepared as described above and run on the CE instrument described above. The mobile phase consisted of 20 mM morpholinoethanesulfonic acid (MES) at pH 6.9/ACN (20:80 v:v), and electroosmotic flow was created by applying a 20 kV potential with a 2 µA current. The results of the separation are shown in FIG. 3.

The efficiency of the first enantiomer was 20,000 (80,000 plates/m; h=2.5). This is significantly higher than the efficiencies obtained for previous chiral CEC capillaries.

Example 2

Figure 4:
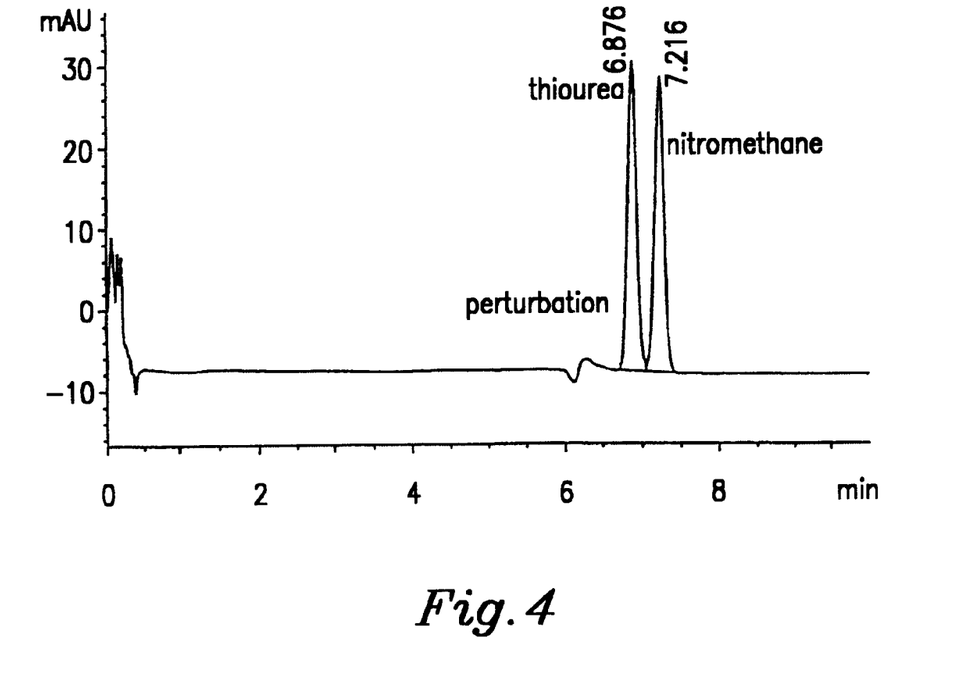
FIG. 4 is a graph of a CEC run to determine a suitable $t_o$ marker.

In order to be able to evaluate the potential of various buffer systems on the stationary phase, potential $t_o$ markers (ACN, Thiourea and nitromethane) were evaluated in separations performed as described in Example 1 to see which would be most suitable for a capillary packed with a 5 µm chiral selector of cellulose tris(3,5-dimethylphenylcarbamate) coated onto silylated silica particles. The results are shown in FIG. 4.

Under the conditions tested, thiourea was less retained than nitromethane, but the perturbation (caused by the difference of ACN content between the sample solution and running electrolyte) was observed 0.8 min before thiourea. It had been known in the art that when using capillaries packed with hydroxypropyl-β-cyclodextrin (HPBCD), the elution order for the perturbation and thiourea switch depended on the concentration of acetonitrile (30 to 50%) such that the perturbation provided a more suitable $t_o$ marker. Over the typical % ACN concentrations used for the capillaries packed as described in Example 1 (50 to 90%), the perturbation always eluted slightly before thiourea and the consistent difference in migration times suggested that thiourea may not be retained by the chiral stationary phase. Despite the latter observation, we decided to use the perturbation as a $t_o$ marker in subsequent examples.

Example 3

The reproducibility of migration time for both electromigration injection and pressure injection for a capillary packed as described in Example 1 were evaluated in this example. Four consecutive injections of benzoin were made by electromigration (12 kV for 10 sec), and likewise by pressure (10 bar for 9 sec), to provide two sets of four separations. Each set utilized different inlet/outlet vials. The separations were otherwise performed as described in Example 1, and the percent relative standard deviations (% RSD) are shown in Table 1.

TABLE 1

| Type of Injection | % RSD for migration times (8 injections) | % RSD (4 areas per set) | % RSD (3 areas per set; area from first injection discarded) |
|---|---|---|---|
| Electromigration (12 kV for 10 sec) | 0.89 | Set 1 - 11.2<br>Set 2 - 13.8 | Set 1 - 0.41<br>Set 2 - 0.58 |
| Pressure (10 bar for 9 sec) | 0.97 | Set 1 - 0.86<br>Set 2 - 0.66 | Set 1 - 0.52<br>Set 2 - 0.43 |

The low % RSD for the migration times confirmed that there was reproducible EOF in the packed capillary. Surprisingly, the peak area precision for four consecutive electromigration injections was less than expected. A closer examination of the results revealed a significantly lower peak for the first separation as compared with the three subsequent separations. When the peak area from the first separation was rejected, the precision improved dramatically and was well within acceptable limits. The peak area precision for all four separations carried out using a pressure injection was within acceptable limits although, as with electrokinetic injection, the precision for pressure injection was slightly better when the peak area from the first separation was rejected.

Example 4

The effect of MES buffer concentration, pH and percent acetonitrile on the separation of neutral chiral compounds 4-phenyl-2-butanol, benzoin and indapamide was investigated in this example. Four consecutive electromigration injections (5 kV for 10 sec) were made. In accordance with the results of Example 3, the first injection was rejected and the mean of the remaining three injections was calculated for each parameter.

MES Concentration

For the first study, the buffer concentration of MES (pH 6.9) was varied between 10 mM and 100 mM. After mixing with 80% ACN, total buffer concentrations of 2 to 20 mM MES were produced. The results of the buffer concentration study are presented in Table 2.

TABLE 2

| Concentration of MES in MES/ACN Mobile Phase | 4-phenyl-2-butanol | | | | | Benzoin | | | | | Indapamide | | | | |
|---|---|---|---|---|---|---|---|---|---|---|---|---|---|---|---|
| | $k_1$ | " | Rs | $N_1$ | $t_2$ (min) | $k_1$ | " | Rs | $N_1$ | $t_2$ (min) | $k_1$ | " | Rs | $N_1$ | $t_2$ (min) |
| 2 mM | 0.403 | 1.14 | 1.19 | 15658 | 7.4 | 0.402 | 1.45 | 2.61 | 7763 | 8.1 | 0.461 | 1.27 | 2.20 | 11858 | 8.2 |
| 4 mM | 0.413 | 1.14 | 1.20 | 15248 | 9.0 | 0.420 | 1.44 | 2.64 | 7712 | 8.7 | 0.468 | 1.26 | 2.20 | 11997 | 8.7 |
| 8 mM | 0.409 | 1.13 | 1.24 | 17298 | 9.1 | 0.413 | 1.43 | 2.90 | 9674 | 9.9 | 0.457 | 1.27 | 2.41 | 14793 | 9.9 |
| 12 mM | 0.419 | 1.13 | 1.34 | 19582 | 10.9 | 0.411 | 1.44 | 3.16 | 11533 | 12.0 | 0.458 | 1.27 | 2.58 | 16732 | 11.9 |
| 16 mM | 0.410 | 1.14 | 1.40 | 21715 | 12.5 | 0.416 | 1.43 | 3.43 | 13769 | 14.0 | 0.456 | 1.27 | 2.74 | 18694 | 13.8 |

Table 2 reveals that as the MES concentration increased, the migration times ($t_2$), efficiency ($N_1$) and resolution (Rs) increased, while the capacity factors ($k'_1$) and selectivity (") remained substantially unaffected.

Though not shown in Table 2, the current through capillary increased from 1.5 to 4.8 μA as the MES concentration increased. The current took a significant time to reach a steady state when the MES concentration was below 5 mM. Further, at an MES concentration of 20 mM the EOF was very erratic, indicating the formation of bubbles in the packed bed.

The increase in migration time was likely a result of the increased buffer concentration causing a compression of the electrical double layer, thereby decreasing the zeta potential at the capillary wall and reducing the EOF. The consistency of the capacity factor and selectivity values indicated that the buffer was not influencing the analytes interaction with the chiral stationary phase. The increase in efficiency resulted in an increase in resolution (Rs) in accordance with Rs √ $\overline{N}$.

The decrease in migration times as the pH increased can be attributed to the increase in zeta potential from the increased silanol density. The stability of the capacity factors and selectivity indicates that in the range investigated, pH played no role in chiral recognition. The increase in efficiency resulted in increased resolution in accordance with Rs √ $\overline{N}$. The cause(s) of the extremely poor peak shapes and efficiencies for the enantiomers of benzoin when the pH was 5.8 or 6.2 is unknown.

These results demonstrate that a higher pH provides faster analysis times and higher resolution. However, the pH chosen for the separation is limited by the buffering capacity of the mobile phase CEC system.

Effect of % ACN

The effect of percent acetonitrile (% ACN) in the mobile phase was studied by performing separations on 4-phenyl-2-butanol, benzoin and indapamide as described in Example 1, except that (1) the % ACN in the mobile phase was varied, and (2) the mobile phase contained 10 mM MES (pH 6.9). The results are shown in Table 4.

TABLE 4

| Percentage ACN in MES/ACN Mobile Phase | 4-phenyl-2-butanol | | | | | Benzoin | | | | | Indapamide | | | | |
|---|---|---|---|---|---|---|---|---|---|---|---|---|---|---|---|
| | $k_1$ | " | Rs | $N_1$ | $t_2$ (min) | $k_1$ | " | Rs | $N_1$ | $t_2$ (min) | $k_1$ | " | Rs | $N_1$ | $t_2$ (min) |
| 80% | 0.417 | 1.13 | 1.36 | 20830 | 11.4 | 0.470 | 1.26 | 2.63 | 18070 | 12.3 | 0.426 | 1.42 | 3.31 | 12662 | 12.4 |
| 70% | 0.600 | 1.13 | 1.50 | 16782 | 14.3 | 0.741 | 1.25 | 3.05 | 14515 | 16.7 | 0.481 | 1.42 | 3.71 | 9316 | 17.4 |
| 60% | 0.948 | 1.13 | 1.82 | 14193 | 18.4 | 1.308 | 1.26 | 3.77 | 12442 | 23.4 | 1.295 | 1.44 | 4.71 | 7588 | 26.5 |

The results demonstrate that, for the neutral compounds tested, higher MES concentrations provide better resolution. However, the amount of current and length of analysis time also need to be considered when choosing a suitable concentration. A total MES concentration of about 10 mM was believed to provide the best compromise between resolution, current and analysis time.

Effect of pH

To evaluate the effect of pH on the chiral separation of neutral compounds, 50 mM MES having pH ranging from 5.8 to 7.1 was mixed with 80% ACN to produce a mobile phase with an MES concentration of 10 mM. The results of the chiral separations of 4-phenyl- 2-butanol, benzoin and indapamide using the various mobile phases and otherwise performed in accordance with Example 1 are shown in Table 3.

Table 4 reveals that as the % ACN decreased, migration times, capacity factors and resolution increased, efficiency decreased, and selectivity was substantially unchanged. Though not shown in Table 4, the current was not affected by decreasing % ACN, and remained at approximately 2.8 μA.

The increase in migration times and capacity factors can be attributed to increased interaction of the mobile phase with the stationary phase as the % ACN is decreased. Although the efficiency decreased as the % ACN was reduced, the resolution increased in accordance with the relation Rs k'/(k'+1).

Figure 5:
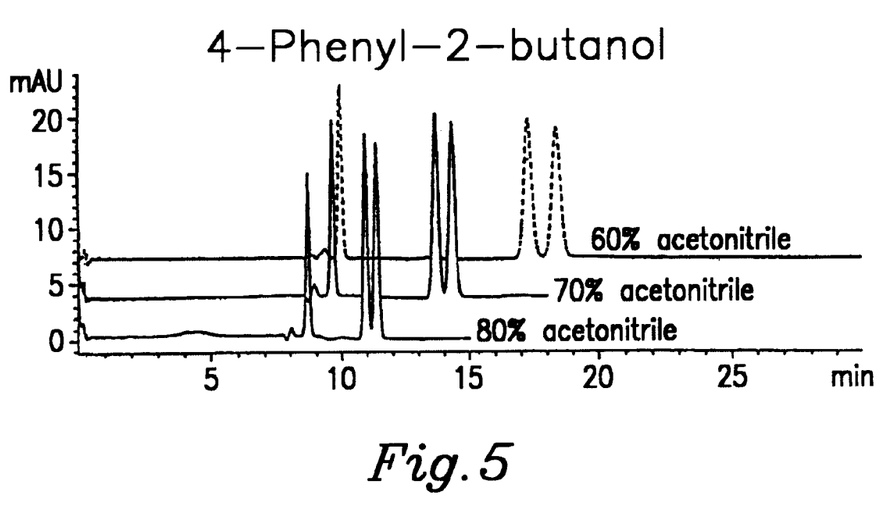
FIG. 5 is a graph of a CEC separation of 4-phenyl-2-butanol performed in accordance with the invention.
Figure 6:
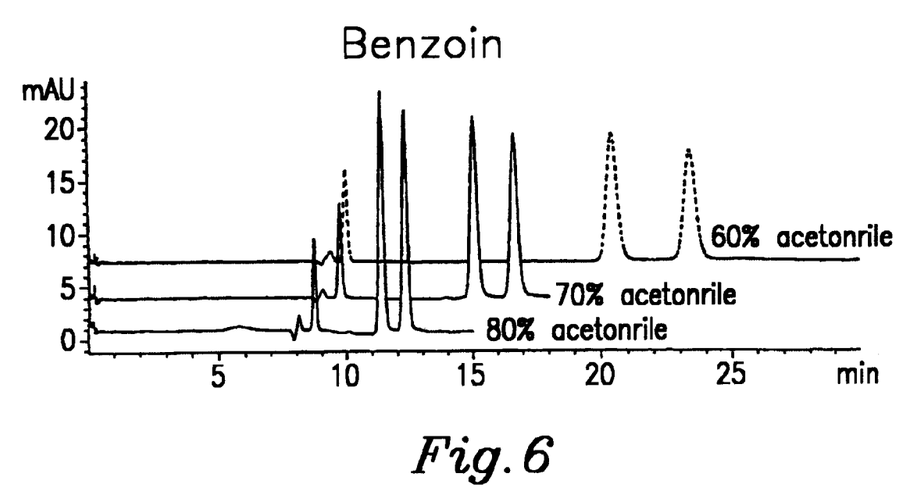
FIG. 6 is a graph of a CEC separation of benzoin performed in accordance with the invention.
Figure 7:
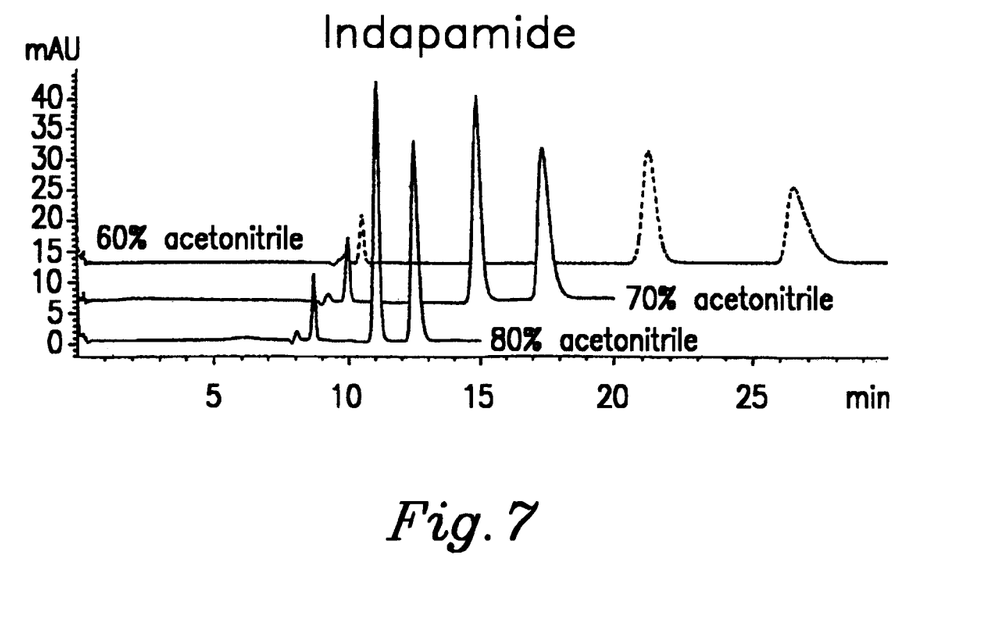
FIG. 7 is a graph of a CEC separation of indapamide performed in accordance with the invention.

As shown in FIGS. 5–7, the % ACN needs to be as low as 60% in order to achieve baseline resolution for 4-phenyl-2-butanol (see FIG. 5), whereas for benzoin and indapamide, 80% ACN provides short analysis times and baseline resolution (see FIGS. 6 and 7, respectively).

Though the invention has been described with reference to specific forms of apparatus and method steps, various

TABLE 3

| pH of MES in MES/ACN Mobile Phase | 4-phenyl-2-butanol | | | | | Benzoin | | | | | Indapamide | | | | |
|---|---|---|---|---|---|---|---|---|---|---|---|---|---|---|---|
| | $k_1$ | " | Rs | $N_1$ | $t_2$ (min) | $k_1$ | " | Rs | $N_1$ | $t_2$ (min) | $k_1$ | " | Rs | $N_1$ | $t_2$ (min) |
| 5.8 | 0.443 | 1.14 | 1.15 | 13361 | 13.2 | 0.504 | 1.26 | * | 2672 | 14.4 | 0.444 | 1.45 | 2.76 | 8047 | 14.5 |
| 6.2 | 0.430 | 1.14 | 1.10 | 12575 | 10.7 | 0.489 | 1.25 | * | 2403 | 11.6 | 0.435 | 1.44 | 2.74 | 7609 | 11.9 |
| 6.7 | 0.412 | 1.13 | 1.21 | 15557 | 9.8 | 0.467 | 1.26 | 2.09 | 10760 | 10.4 | 0.422 | 1.46 | 2.87 | 8604 | 10.8 |
| 7.1 | 0.413 | 1.13 | 1.31 | 18787 | 9.4 | 0.467 | 1.26 | 2.54 | 16090 | 10.0 | 0.419 | 1.44 | 3.05 | 10146 | 10.1 |

*extremely poor peak shape, hence very low resolution

Table 3 reveals that as pH increased, resolution and efficiency increased, migration times decreased, and capacity factors and selectivity were unaffected. Though not shown in Table 3, the increasing pH had no significant effect on the current, which stayed at approximately 2.7 μA.

changes, modifications, additions and omissions may be made without departing from the spirit and scope of the invention defined in the appended claims.

We claim:

1. A method for separating a mixture of at least two chemical compounds by capillary electrochromatography which produces a reduced plate height of 3 or less, the steps which comprise:

loading a frit material into a capillary, said capillary having first and second portions, said loading occurring in at least said first portion of said capillary;

sintering said frit material at said first portion of said capillary to form a first retaining frit;

removing substantially all unsintered frit material from said capillary;

loading a packing material into said capillary between said first retaining frit and said second portion of said capillary to form a stationary phase, said packing material comprising a silica gel substrate coated with a polysaccharide chiral selector;

loading said frit material in said second portion of said capillary adjacent to said stationary phase;

sintering said frit material to form a second retaining frit adjacent to said stationary phase;

removing substantially all unsintered frit material from said capillary;

introducing said mixture into said capillary at one of said retaining frits; and inducing migration of said mixture across said stationary phase by applying a voltage across said capillary, wherein at least one of said chemical compounds is separated from said mixture by exhibiting an electroosmotic flow velocity different from other said chemical compounds in said mixture.

2. A method for separating a mixture of at least two chemical compounds by capillary electrochromatography which produces a reduced plate height of 4 or less, the steps which comprise:

loading a frit material into a capillary, said capillary having first and second portions, said loading occurring in at least said first portion of said capillary;

sintering said frit material at said first portion of said capillary to form a first retaining frit;

removing substantially all unsintered frit material from said capillary;

loading a packing material into said capillary between said first retaining frit and said second portion of said capillary to form a stationary phase, said packing material comprising a silica gel substrate coated with a polysaccharide chiral selector;

loading said frit material in said second portion of said capillary adjacent to said stationary phase;

sintering said frit material to form a second retaining frit adjacent to said stationary phase;

removing substantially all unsintered frit material from said capillary;

introducing said mixture into said capillary at one of said retaining frits; and inducing migration of said mixture across said stationary phase by applying a voltage across said capillary, wherein at least one of said chemical compounds is separated from said mixture by exhibiting an electroosmotic flow velocity different from other said chemical compounds in said mixture.

3. The method according to claim 2, wherein said polysaccharide chiral selector is linear.

4. The method according to claim 2, wherein said polysaccharide chiral selector is selected from the group consisting of cellulose, cellulose derivatives, amylose, and amylose derivatives.

5. The method according to claim 2, wherein said polysaccharide chiral selector is cellulose tris(3,5-dimethylphenylcarbamate).

6. The method according to claim 2, wherein said step of inducing migration further comprises applying a pressure gradient across said capillary.

7. The method according to claim 2, wherein said capillary comprises at least one material selected from the group consisting of fused silica, nylon, polyurethane, polyethylene and polytetrafluoroethylene.

8. The method according to claim 2, wherein said capillary is a fused silica capillary.

9. The method according to claim 2, wherein said mixture comprises chiral compounds.

10. The method according to claim 2, wherein said mixture comprises achiral compounds.

11. The method according to claim 2, wherein said substrate is a silica product.

12. The method according to claim 2, wherein said substrate is a silylated silica product.

13. The method according to claim 2, wherein said frit material is an octadecyl silica product.

14. The method according to claim 2, wherein said loading of said packing material into said capillary comprises pumping a slurry of said packing material into said capillary at a pressure of no greater than about 430 bar.

15. The method according to claim 2, wherein said loading of said packing material into said capillary comprises electrokinetically pumping a slurry of said packing material into said capillary.

16. The method according to claim 2, wherein said reduced plate height is 2.5 or less.

* * * * *

UNITED STATES PATENT AND TRADEMARK OFFICE
CERTIFICATE OF CORRECTION

PATENT NO. : 6,224,775 B1　　　　　　　　　　　　　　　　　　　　Page 1 of 1
DATED : May 1, 2001
INVENTOR(S) : Foley et al.

It is certified that error appears in the above-identified patent and that said Letters Patent is hereby corrected as shown below:

Column 5,
Line 11, please change "dp" to -- $d_p$ --; and
Line 40, "(HPBCD)", the "B" should be replaced with the beta sign -- $\beta$ --.

Column 7,
Line 20, please change "Rs $\sqrt{N}$" to -- Rs $\propto$ $\sqrt{N}$ --.

Column 8,
Line 7, please change "Rs $\sqrt{N}$" to -- Rs $\propto$ $\sqrt{N}$ --;

Line 42, please change "Rs k'/(k' + 1)" to -- Rs $\propto$ k'/(k' + 1) --.

Signed and Sealed this

Second Day of April, 2002

Attest:

JAMES E. ROGAN
*Attesting Officer*　　　*Director of the United States Patent and Trademark Office*